United States Patent [19]

Memeger, Jr.

[11] Patent Number: 5,189,160
[45] Date of Patent: Feb. 23, 1993

[54] CYCLIC AROMATIC AMIDE OLIGOMERS

[75] Inventor: Wesley Memeger, Jr., Wilmington, Del.

[73] Assignee: E. I. Du Pont de Nemours and Company, Wilmington, Del.

[21] Appl. No.: 690,758

[22] Filed: Apr. 24, 1991

[51] Int. Cl.⁵ .......................................... C07D 259/00
[52] U.S. Cl. ................................. 540/460; 522/176
[58] Field of Search .................................... 540/460

[56] References Cited

U.S. PATENT DOCUMENTS

| | | | |
|---|---|---|---|
| 4,808,754 | 2/1989 | Guggenheim et al. | 564/428 |
| 4,837,298 | 6/1989 | Cella et al. | 528/352 |
| 4,868,279 | 9/1989 | Guggenheim et al. | 528/324 |

OTHER PUBLICATIONS

Kevin Randall Stewart, Polymer Preprints 30(2), 140 (1989).
D. J. Brunelle et al., Polymer Preprints 30(2), 569 (1989).
Eugene P. Boden et al., Polymer Preprints 30(2), 573 (1989).
Kevin Randall Stewart, Polymer Preprints 30(2), 575 (1989).
T. L. Guggenheim et al., Polymer Preprints 30(2), 138 (1989).

*Primary Examiner*—Robert T. Bond

[57] ABSTRACT

This invention concerns cyclic aromatic amide oligomer compositions and a process for preparing such cyclic oligomers.

20 Claims, 4 Drawing Sheets

CYCLIC AROMATIC AMIDE OLIGOMERS

BACKGROUND OF THE INVENTION

1. Field of the Invention

This invention concerns cyclic para-oriented aromatic amide (aramid) oligomers and the ring opening polymerization thereof and a process for preparing cyclic oligomers.

2. Technical Review

Aromatic polyamides (aramids) are generally synthesized by the reaction of an aromatic diacid chloride with an aromatic diamine in an appropriate solvent. Nomex ® aramid (poly(m-phenylenediamine-m-phthalamide) and Kevlar ® aramid (poly(p-phenylenediamine-t-phthalamide) are two examples of products based on polymers prepared in this manner. Ring opening polymerization could simplify aramid polymerization processes versus "acid chloride plus amine" processes because no by products would be eliminated in the course of the polymerization reaction. Thus, no hydrogen chloride by product would be formed which would eliminate corrosion potential, a major concern with current aramid processes.

A necessary prerequisite to the practice of ring opening polymerization is a process route to cyclic oligomers of the monomers that are the components of the desired polymer. Cyclic oligomers and ring opening polymerization are known in a variety of polymeric systems, for example, aliphatic polyesters, silicones, epoxides, and a limited number of selected polyamides T. L. Guggenheim et al., Polymer Preprints 30(2), 138 (1989), describe the synthesis of cyclic amide oligomers from diamines containing the spiro bis indane group reacted with isophthaloyl chloride and further report the copolymerization of this cyclic aramid oligomer with caprolactam. The authors further report that simpler diamines, e.g. m-phenylene diamine and 2,2-bis-(4-aminophenyl)propane, when reacted with isophthaloyl chloride or terephthaloyl chloride, afforded no appreciable amount of cyclic oligomer. Functional groups separated by para phenylene moities were believed to have a negative effect on cyclic oligomer formation.

Similar cyclic amide oligomers, all based on spiro bis indane derivatives, are described in U.S. Pat. Nos. 4,808,754, 4,837,298 and 4,868,279. U.S. Pat. No. 4,808,754 describes a process for the preparation of cyclic polyamide oligomers by the reaction of spirobiindane diamines, including spirobiindane bisphenol bisphenol dis-aminophenoxy ethers with dicarboxylic acid chloride. '754 claims certain spirobiindane bis-aminophenoxy ethers. U.S. Pat. No. 4,837,298 describes a process for preparing cyclic imides by the reaction of a bis(dicarboxyphenyl) sulfide or functional derivitive thereof with a diamine having a spirobiindane nucleus. U.S. Pat. No. 4,868,279 describes a spiro(bis)indane copolyamide and the preparation thereof by the reaction of monocyclic spiro(bis)indane polyamide oligomers with lactams in the presence of basic reagents.

SUMMARY OF THE INVENTION

This invention provides cyclic aramid oligomers of the structure I wherein:

A, B, D, and E, independently are divalent aromatic groups such as p-phenylene, m-phenylene, 3,3'-biphenylene, 4,4'-biphenylene, 1,4-naphthalenediyl, 2,6-naphthalenediyl, oxy-3,4'- and oxy-4,4'-diphenyldiyl and the corresponding methylene and sulfone analogs, and R is alkyl up to 8 carbon atoms or cycloalkyl up to 8 carbon atoms or aralkyl with the ar- portion being phenyl or naphthyl and the alkyl having up to 8 carbon atoms, and n is an integer from 0 to about 12.

A subclass of the general structure I consists of those cyclic aramid oligomers where all aromatic units are derived from benzene or substituted benzene, e.g.

wherein:

R is alkyl or cycloalkyl up to about 8 carbon atoms, or aralkyl with the ar- portion being phenyl or naththyl and the alkyl having up to about 8 carbon atoms;

X is hydrogen, alkyl up to about 8 carbon atoms, halide, or alkoxy up to about 8 carbon atoms, Y is defined the same as is X, and n is an integer ranging from 0 to about 12.

This invention also provides AB analogues of I of the structure II:

wherein A, B and R are as defined above and n is an integer from 1 to about 12.

Also provided is a process for the preparation of cyclic oligomers of the above structure I, which process comprises reacting monomeric components of the structures ClCO-A-COCl and ClCO-D-COCl with monomeric components of the structure RHN-B-NHR and RHN-E-NHR, wherein A, B, D and E are as defined above.

Also provided is a process for the preparation of cyclic oligomers of the above structure II, which process comprises reacting 2 or more monmeric components of the structures ClCO-Q-NHR wherein Q is A, B, C, D or E.

Also provided is a process for the preparation of high molecular weight aramid polymers which method comprises the polymerization of cyclic oligomers as described above making use of a nucleophilic catalyst.

DETAILED DESCRIPTION OF THE INVENTION

This invention provides cyclic aramid oligomers of the structure wherein:
A, B, D, and E, independently are divalent aromatic groups such as p-phenylene, m-phenylene, 3,3'-biphenylene, 4,4'-biphenylene, 1,4-naphthalenediyl, 2,6-naphthalenediyl, oxy-3,4'- and oxy-4,4'-diphenyldiyl and the corresponding methyl and sulfonyl analogs, R is alkyl or cycloalkyl up to about 8 carbon atoms, or aralkyl with ar- portion being phenyl or naththyl and with the alkyl portion up to about 8 carbon atoms; and n is an integer from 0 to about 12.

A subclass of this general structure consists of those cyclic aramid oligomers where all aromatic units are derived from benzene or substituted benzene, e.g.

wherein:
R is alkyl or cycloalkyl up to about 8 carbon atoms, or aralkyl with ar- portion being phenyl or naphthyl and the alkyl portion up to about 8 carbon atoms;
X is hydrogen, alkyl up to about 8 carbon atoms, halide, or alkoxy up to about 8 carbon atoms,
Y is defined the same as is X, and
n is an integer ranging from 0 to about 12.

This invention also provides AB analogues of I of the structure II:

wherein A, B and R are as defined above and n is an integer from 1 to about 12.

Also provided is a process for the preparation of cyclic oligomers of the above structure I, which process comprises reacting monomeric components of the structures ClCO-A-COCl and ClCO-D-COCl with monomeric components of the structure RHN-B-NHR and RHN-E-NHR, wherein A, B, D and E are as defined above.

Further provided is a process for the preparation of cyclic oligomers of the above structure II, which process comprises reacting 2 or more monomeric components of the structure ClCO-Q-NHR wherein Q is A, B, C, D or E, and R are as defined above.

Also provided is a process for the preparation of high molecular weight aramid polymers which method comprises the polymerization of cyclic oligomers as described above, using a preferred very highly nucleophilic catalyst such as 1-methyl-3-butylimidazole-2-thione. The effect of this catalyst can be accentuated by using a proton source such as phenyl phosphinic acid in the reaction mixture. Other nucleophilic agents such as thiourea and aromatic amines are also effective catalysts, especially when used with a proton source. A preferred catalyst is N-benzoyl-p-phenylene diamine, possibly due to its high boiling point. It is preferred that such catalysts have a high boiling point. Strong acids such as benzenesulfonic acid, phenyl phosphinic and 2-(2'-pyridyl)ethylphosphonic acid are also effective catalysts. Where strong acids are used, dealkylation can occur resulting in polymers with higher $T_g$, often a desirable result.

The cyclic aramid oligomers provided by the present application are useful to prepare high molecular weight aramid polymers, for example, high molecular weight poly(N-substituted-p-phenylene-terephthalamide) via ring opening polymerization. The cyclic aramid oligomers are also useful in exerting a strong plasticizing influence on linear aramid polymers. The high molecular weight poly(N-substituted-p-phenylene-terephthalamide) prepared via ring opening polymerization is useful for the preparation of fibers, coatings, films, foams, moldings and matrices for composites.

In the structure RHN-B-NHR and RHN-E-NHR, wherein B and E are as defined above, R is alkyl or cycloalkyl up to about 8 carbon atoms or aralkyl with ar- portion being phenyl or naphthyl and the alkyl portion up to about 8 carbon atoms. It is preferred that R be from 3 to 8 carbons; 4 to 6 carbons is more preferred. R having 4 carbons, e.g. sec butyl is most preferred.

The reaction of ClCO-A-COCl and ClCO-D-COCl, where A and D are as defined above, with RHN-B-NHR and RHN-E-NHR is carried out in aprotic organic solvents, such as toluene, xylene, o-dichlorobenzene, 1,3,5-trichlorobenzene, tetrahydrofuran and methylene chloride. Preferred solvents are o-dichlorobenzene, toluene, 1,3,5-trichlorobenzene. The most preferred solvent is o-dichlorobenzene. The reaction of ClCO-A-COCl and ClCO-D-COCl can be accelerated by using a tertiary amine base, such as triethyl amine, pyridine or 4-dimethylaminopyridine. The most preferred base is 4-dimethylaminopyridine.

The reaction of ClCO-A-COCl and ClCO-D-COCl with RHN-B-NHR and RHN-E-NHR can be carried out at temperatures from about 40° to about 300° C., more preferably at temperatures from about 100° C. to about 200° C.

The reaction of 2 or more monomeric units of the structure ClCO-Q-NHR, wherein Q is A, B, C, D, or E, and R is as defined above, is carried out using the same solvents and under the same temperature conditions as above.

EXAMPLES

EXAMPLE 1

Preparation of N,N'-di-s-butyl-p-phenyleneterephthalamide Cyclic Oligomers.

To a 3 L 3 necked round bottom flask equipped with a mechanically driven stirrer, dry nitrogen line, and two dropping funnels is added 900 mL of o-dichlorobenzene (ODBC). The o-dichlorobenzene is heated to 80° C. whereupon 22.0 g (0.1 mol) of N,N'-di-s-butyl-p-phenylene amine in 450 mL of ODBC and 20.3 g terephthaloyl chloride in 450 mL ODBC are added dropwise over a 3 hr period.

The cloudy mixture is heated to reflux and stirred for 1 week. The mixture becomes translucent but not clear during heating. The mixture is allowed to cool and the ODBC is removed on a rotary evaporator under pump vacuum using a 100° C. oil bath. The yield is 36.7 g, 105% of theoretical the excess due to residual ODBC according to thermogravimetric analysis. The product has an inherent viscosity of 0.058 dL/g (0.5% in conc. H2SO4 at 30° C.). The material is found to be 86% soluble in toluene of which the gel phase permeation chromatography shows no high molecular polymer. The reverse phase HPLC analysis of the material shows that the material contains a multiplicity of peaks which are found by FAB MS to correspond to cyclic oligomers of N,N'-di-s-butyl-p-phenyleneterephthalamide. In addition, peaks are found which correspond to cyclic oligomers where one or more of the s-butyl groups is eliminated during the reaction. Loss of a s-butyl group is facilitated by acid, in this case the HCl by-product from the reaction.

Fractionation and Characterization of Cyclic N,N'-di-s-Butyl-p-phenyleneterephthalamide Oligomers A normal phase HPLC of the product was done on a Zorbax ® silicon gel column using methanol and chloroform as mobile phases. A FAB MS analyses of fractions 1 to 7 of the product was carried out. Fractions 1 to 3 are clean fractions of cyclic dimer (M+H of 701), trimer (M+1 of 1051) and tetramer (M+H 1402), respectively. The FAB MS of fraction 4 shows a mixture of cyclic pentamer (M+H 1753), tetramer and trimer (minus - s-butyl M+H 996) The FAB MS of fraction 5 was shown as a dominant peak for cyclic hexamer at M+H of 2103. The FAB MS of fraction 6 was shown as a mixture of heptamer (M+H 2454) and hexamer. The FAB MS for fraction 7 shows a mixture of hexamer, heptamer, octamer (M+H 2805), nonamer (M+H 3155), decamer (M+H 3506) and undecamer (M+H 3956). In this fraction, cyclic octamer is the major component.

Figure 1A:
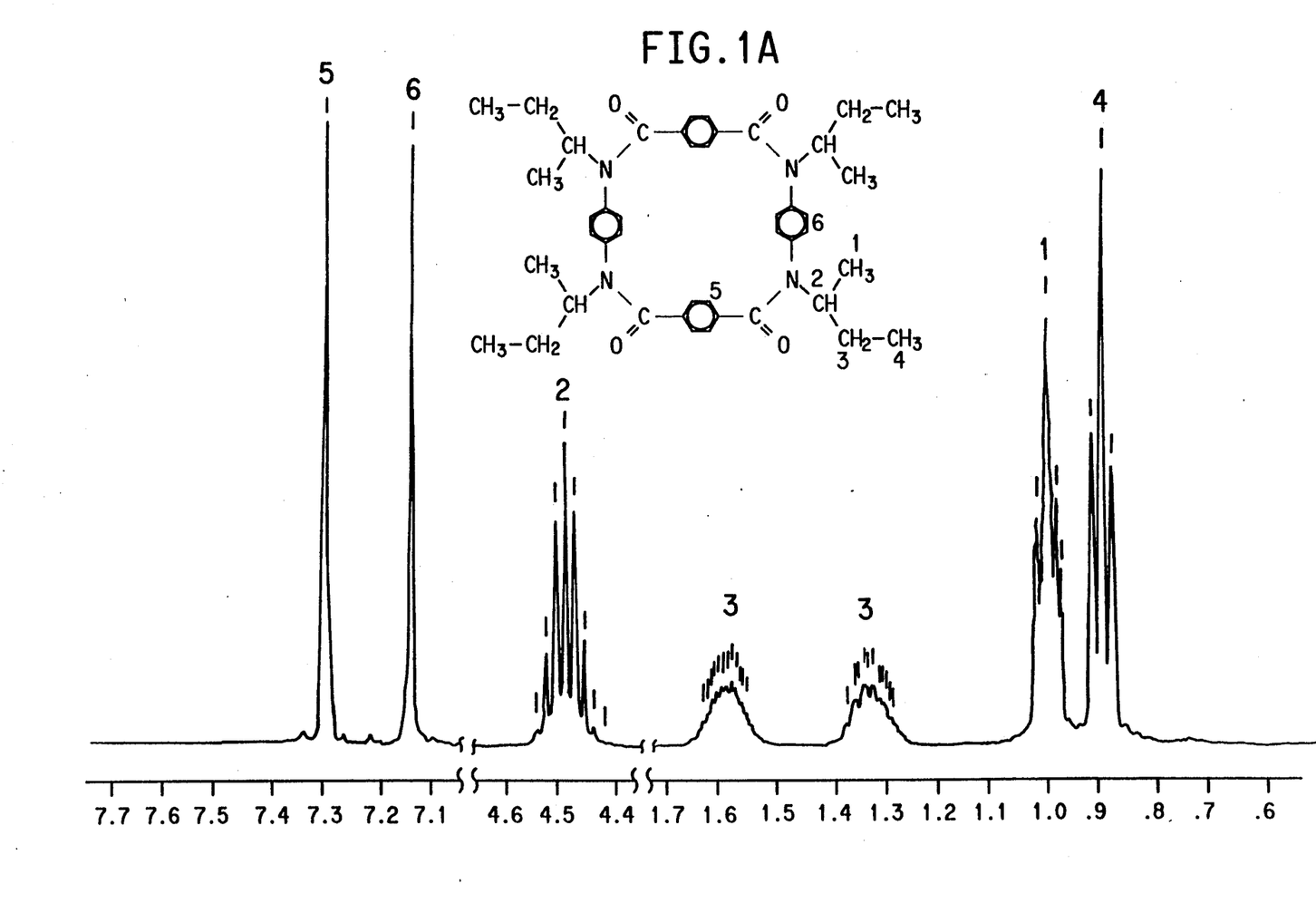
FIG. 1(a) through FIG. 1(c) show $^1$H NMR spectra of N,N'-di-s-butyl-p-phenylene terephthalamide cyclic dimer.
Figure 1B:
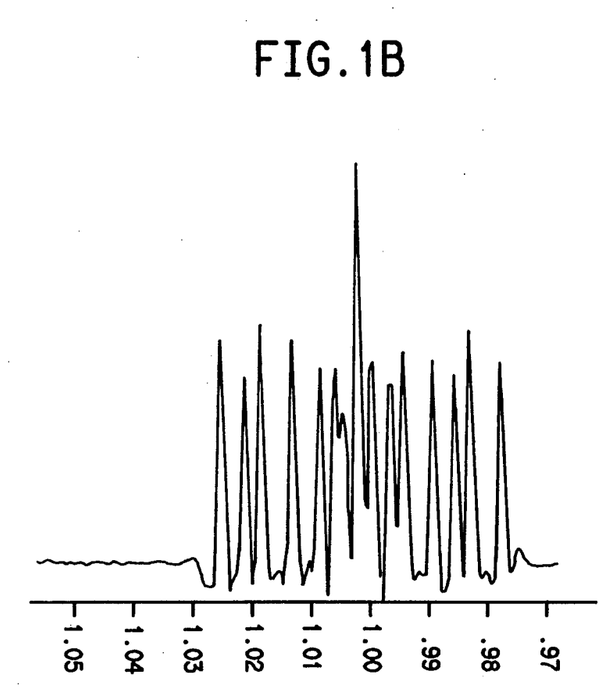
Figure 1C:
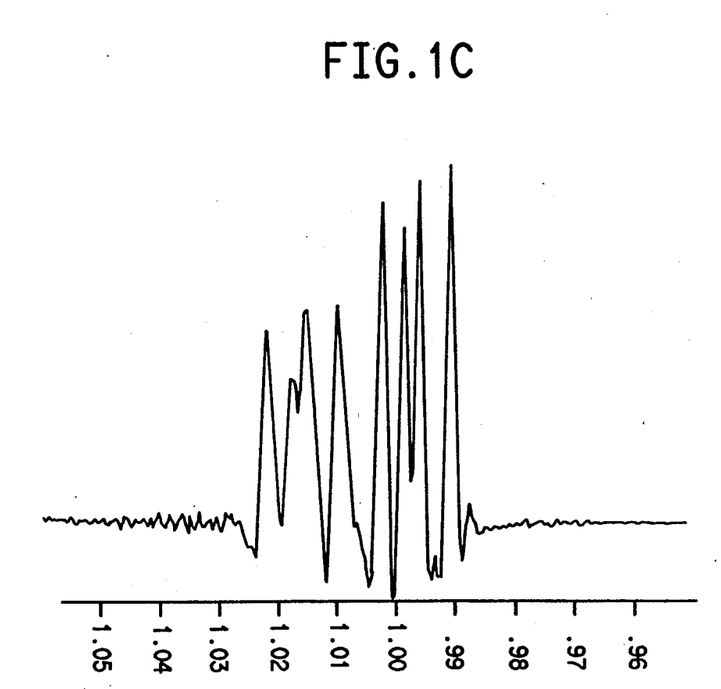
Figure 2:
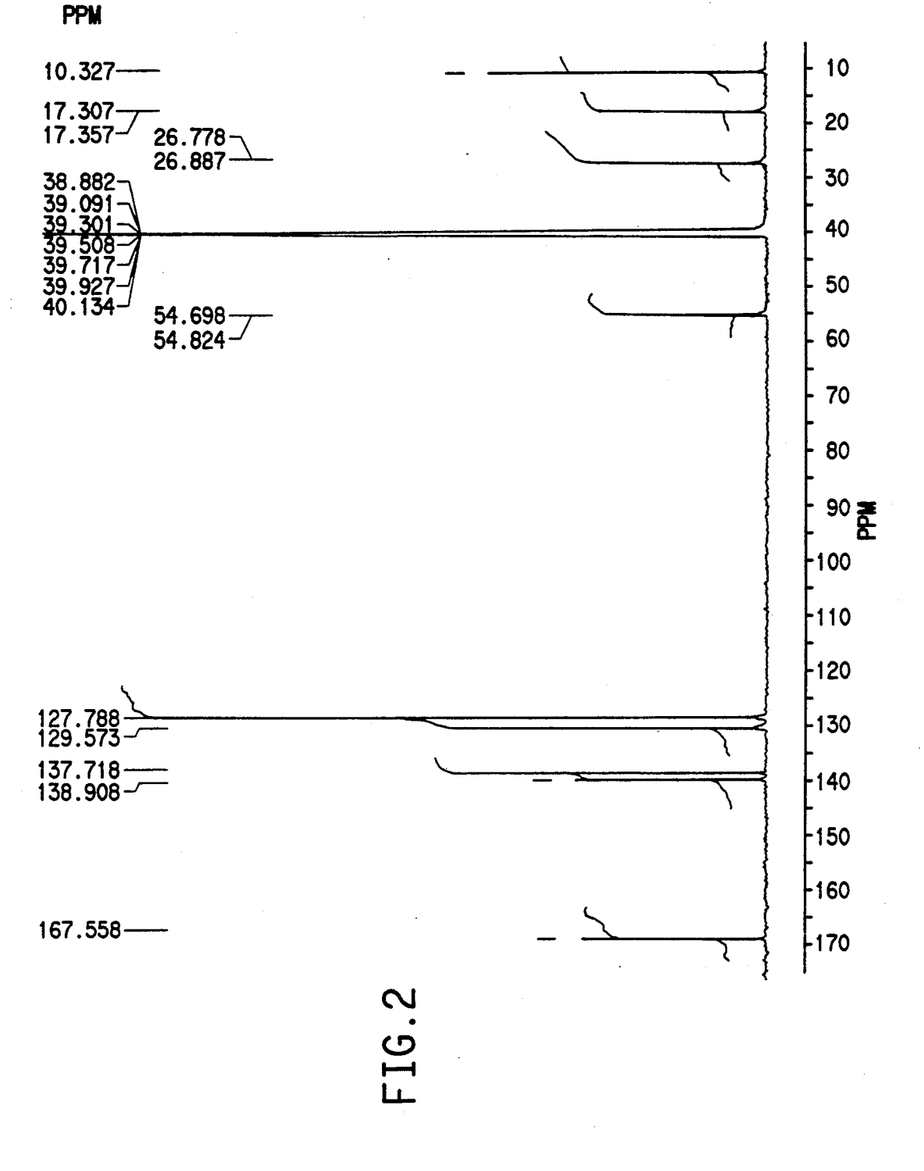
FIG. 2 shows a $^{13}$C NMR spectrum of N,N'-s-butyl-p-phenylene terephalamide cyclic dimer.

A Proton NMR analysis of the above fraction 1, the cyclic dimer was carried out at 120° C. in d6 DMSO using a Brucker WM-400 NMR spectrometer. (The spectrum at room temperature is broad due to an apparent lack of mobility in the molecule). FIG. 1a shows the 1 H NMR spectrum. The s-butyl group exhibits the following resonances: 353-357 Hz (12 H, 4 methyl groups attached to methylenes, t); 390-409 Hz (12 H, 4 methyl groups attached to methines - m 15 lines, the center one of double intensity, FIG. 1b, decreases to 8 (FIG. 1c) when the asymmetric methine protons are irradiated indicating that there are 8 magnetically distinguishable stereoisomers present—a 2 D J resolved experiment showed the methyl group protons experience only a single splitting from the methine proton); 516-548 Hz and 620-615 Hz (8 H, 4 methylene groups attached to methines, two m); 1768-1816 (4 H, 4 methine groups, m); 7.14 (8 H on p-phenylene diamine rings, s) vs 2.50 for DMSO; 7.29 (8 H on terephthaloyl rings, s). The spectrum shows the material has only two kinds of aromatic rings and the correct ratio of aliphatic to aromatic protons consistent with a cyclic dimer structure. The 13 C NMR spectrum (FIG. 2) is also consistent with cyclic dimer. The 1 H NMR spectrum of the cyclic trimer also shows a complex pattern for the methyl group attached to the methine due to number of stereoisomers, but here the lines are less sharp than for the cyclic dimer indicative of rapid isomerization.

EXAMPLE 2

Preparation of N,N'-di-s-butyl-p-phenyleneterephthalamide Cyclic Oligomers.

To a 3 L 3 necked round bottom flask equipped with a mechanically driven stirrer, dry nitrogen purge tube and two dropping funnels was added 900 mL of o-dichlorobenzene (ODBC). The o-dichlorobenzene is heated to 80° C. whereupon 22.0 g (0.1 mol) of N,N'-di-s-butyl-p-phenylene amine in 450 mL of ODBC and 20.3 g terephthaloyl chloride in 450 mL ODBC are added dropwise over a 3 hr period. A nitrogen purge tube with a coarse fritted glass tip is inserted beneath the surface of the reaction mixture and the boil bath temperature is increased to 190° C. and the mixture stirred for 5 days. The translucent almost clear mixture is allowed to cool to room temperature and the ODCB is removed on a rotary evaporator. The solid obtained is transferred to a Soxhlet extractor and extracted for 4 days with toluene. The grayish residue left in the thimble is dried under a stream of nitrogen, ground up and further air dried. Yield 8.6 g (Sample A). The clear toluene fraction is placed on a rotary evaporator and the toluene removed under pump vacuum giving a foamy light yellow solid which smells of ODBC. The solid is ground up in a motar with pestle and is further dried at about 90° C. on a rotary evaporator. Yield 22.8 g. (Sample B). The inherent viscosity (measured as in Example 1) is 0.22 for Sample A and 0.05 for Sample B. FAB MS analysis indicates Sample A contains unextracted cyclic dimer, trimer and tetramer in addition to linear oligomers while Sample B showed clear peaks for cyclic dimer, trimer, tetramer, pentamer, hexamer and heptamer. Preparative HPLC shows that Sample B contained 9% cyclic dimer, 32% cyclic trimer, the remainder consisting of higher cyclic oligomers. The elemental analysis of cyclic trimer ($C_{66}H_{78}N_6O_6$, MW: 1051.6) for C, H, N, respectively, are 75.42, 7.62, 8.02 (calculated, 75.44, 7.48, 8.00).

EXAMPLE 3

Ring Opening Polymerization of N,N'-Di-s-butyl-p-phenyleneterephthalamide Cyclic Trimer To a 10 mL round bottom flask equipped with a 3 necked adapter with nitrogen line, condenser with drying tube and mechanically driven glass paddle stirrer is added 0.350 g N,N'-di-s-butyl-p-phenyleneterephthalamide Cyclic Trimer and 0.005 g of 1-methyl-3-butylimidazole-2-thione (MeBuImT). After sweeping with nitrogen for a few min, the flask is placed in a 260° C. oil bath without stirring. Within a few min a clear slightly viscous melt is obtained. The rate of stirring is set at a few RPM sufficient to mix the ingredients. After 30 min the stirrer is stopped and the temperature raised to 265° C. and is held for 2 hrs at which point an increase in viscosity is perceptible. Stirring on an intermittent basis is continued for 4 hrs. The moderately viscous melt is allowed to cool giving a caramel colored clear solid. The recovered yield is 0.303 g. The inherent viscosity is 0.57 (measured in same manner in conc. sulfuric acid as in Example 1). The polymer exhibits a melting point of 284° C. on a gradient hot bar. Fibers can be pulled from a melt pool of the product on the surface of a gradient hot bar at 300° C. The FTIR spectrum exhibits absorption for the carbonyl group at 1645-cm and s-butyl absorption at 2820, 2920 and 2970 -cm and virtually no NH absorption all consistent for poly(N,N'-di-s-butyl-p-phenyleneterephthalamide) and unconverted cyclic trimer. The latter is evident from a spot with $R_f$ of 0.57 on a Kieselgel 60 F 254 thin layer chromatography plate using chloroform to spot and ethyl acetate to develop. (Unlike the cyclic trimer, the polymer is not completely soluble in toluene for thin layer chromatography). During the TLC, the polymeric fraction remains at the origin.

Figure 3:
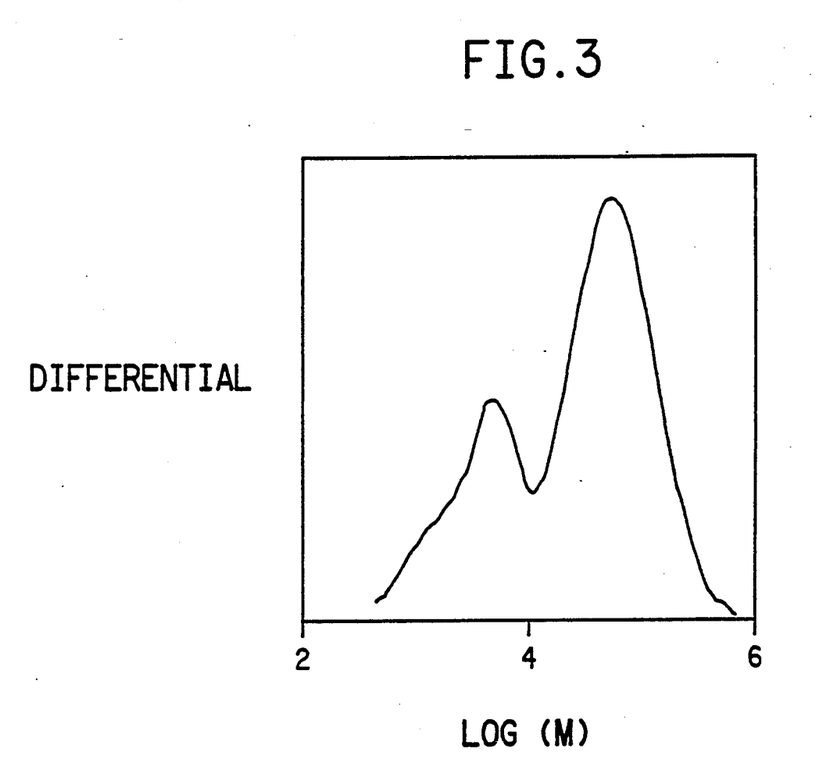
FIG. 3 shows the Gel phase chromatogram of log molecular weight versus differential of Poly(N,N'-di-s-butyl-phenyleneterepthtalamide from N,N'-di-s-butyl-p-phenyleneterephtalamide) cyclic trimer.

The weight average molecular weight (Mw) and number average weight (Mn) were determined on the above sample at 0.1% in hexafluroisopropanol using a Du Pont Zorbax ® PSM Bimodal silica column with a differential refractive index detector. FIGS. 3 shows log molecular weight versus differential. Mw and Mn (versus a polyethylene terephthalate standard) from the curves are found to be 61,100 and 7,410 giving a polydispersity of 8.2. When the low molecular fraction is subtracted out (approximately 30%), the higher molecular weight fraction is calculated to have a Mw of 78,600 and Mn of 48,700 giving a polydispersity of 1.6. A run without catalyst is shown in Table 1A, listed under the Example 3 control, which gave very little conversion of the cyclic trimer to polymer.

EXAMPLE 4

Ring Opening Polymerization of N,N'-Di-s-butyl-p-phenyleneterephthalamide Cyclic Tetramer Using the apparatus described in Example 3, 0.350 g. of cyclic tetramer containing a small amount of cyclic trimer by TLC analysis and 0.005 g 1-methyl-3-butylimidazole-2-thione are treated as follows. The flask is placed in a 250° C. oil bath where an off-white clear melt is formed within a minute. The temperature is raised to 272° C. over the next 10 min. The temperature is lowered over the next 8 min to 267° C. where the melt becomes pasty and further to 260° C. over 10 min. The temperature is raised to 270° C. where a solid forms within a few minutes. The heat is removed and an aliquot of the solid is taken and exhibits a melting point of 305° C. on a gradient hot bar. Thin layer chromatography as described in Example 3 shows incomplete conversion of the cyclic tetramer. The oil bath is replaced by a Woods metal bath and heating is carried out at 305° to 313° C. for 15 min then for 5 min at 313° to 310° C. for 5 min and finally for 15 min at 310° C. After cooling to room temperature a light tan solid weighing 0.230 is collected. The material exhibits an inherent viscosity of 0.22 versus 0.09 for the cyclic tetramer when measured as described in Example 1. The material exhibits a melting point of 270° C. on a gradient hot bar.

EXAMPLE 5

Ring Opening Polymerization of N,N'-Di-s-butyl-p-phenyleneterephthalamide Cyclic Trimer Using 1-methyl-3-butylimidazole-2-thione Catalyst and Phenyl Phosphinic acid Co-catalyst To the appratus described above, 0.175 g (0.166 m mol) of cyclic trimer, 0.00020 g (0.118 m mol) 1-methyl-3-butylimidazole-2-thione and 0.0015 g (0.0095 m mol) phenyl phosphinic acid were added. Heating was begun at 275° C. and a melt formed within a few minutes. Heating was continued for 45 minutes during which time the temperature fluctuated between 265° C. and 271° C. Some time during the next 2.75 hours, the melt became viscous and translucent to opaque. At this point, the bath temperature was raised to 288° C. over about 5 minutes. The mixture did not flow at this temperature. After 30 minutes more of heating at 282° C. to 289° C., heat was removed and a yellow solid was obtained. When the flask was detached from the apparatus, a foamy yellow solid adhered to the stirrer. This material was somewhat friable but integral and also nearly uniformly foamed throughout. The surface of the material had shear lines due to stirring in the viscous state before solidification occurred. A flexible film was found at the bottom of the flask which became detached when pushed with a spatula. This thin film, which weighed 10 mg, appeared to have been formed as the viscous melt was sheared against the bottom of the flask. The above foamy product was not soluble in toluene as is the starting trimer. The material softened in chloroform and the extract spotted on a TLC plate. There was only a faint spot at the $R_f$ corresponding to a cyclic trimer. A significant spot appeared at the origin, undoubtedly polymeric. The polymer had an inherent viscosity of 0.43. $M_w$ and $M_n$ (versus a polyethylene terephthalate standard) were found to be 38,200 and 9,220, respectively, giving a polydispersity of 4.2. A FTIR spectrum showed that appreciable dealkylation occurred during or after the ring opening polymerization.

EXAMPLE 6

Formation of Tough Drawable Film of Polymer from Ring Opening Polymerization of the Cyclic Trimer.

The Cyclic Trimer (0.175 g), 0.002 g of 1-methyl-3-butyl-imidazole-2-thione and 0.0015 g phenyl phosphinic acid were added to the apparatus described in Example 3 and the system swept free of air with nitrogen bleed. A 275° C. Woods metal bath was raised and stirring was begun and within 5 min. a clear melt was formed. The clear melt was then stirred at 275° C. for 5.5 h. during which there was a large increase in the melt viscosity to the point where the the melt became unstirrable. At this point the temperature was raised to 290° C. and held for 45 min. Upon disassembling the apparatus, a tough foamy product was obtained with a smooth film on the bottom surface next to the glass surface. The other surfaces were also smooth but bore shear lines and folds from the stirrer action. There was also present a tough film which adhered to the bulk of the polymer especially that connected to the smooth area between the reactor wall and the bulk of the polymer. This film could be peeled off and was tough, flexible and creasable. The total recovered yield was 0.120 g. The inherent viscosity was 0.82. Thin layer chromatrography analysis indicated that the conversion of cyclic trimer to polymer was quantitative. The film had a PMT>310° C. Short lengths (1–3 cm) of the films were striped from the filmy part of the sample and were drawn up to 2.5× at 354° C. by holding the ends of the strips with tweezers and passing over a 1.9 cm diameter heated rod. The tough drawn film exhibited an X-ray orientation angle of 33° 2 $\theta$.

Table 1A and B, below, show conditions used for ring opening polymerization of N, N'-Diphenyleneterephthalamide cyclic oligomers and results obtained from the controls for Examples 3 and 12. Examples 3, 4, 5, and 6 and controls were carried out, as described in detail above, although the controls were carried out without catalyst.

TABLE 1A

| | Cyclic Homologue | Cyclic homologue g., m mol. | Catalyst | Catalyst mg., umol. | Temp.C | Temp.h |
|---|---|---|---|---|---|---|
| Ex. 1 | Trimer | | | | | |
| Ex. 3 Control | Trimer | | Control | | 265 | 6 |
| | | | | | 260–170 | 0.25 |
| | | | | | 305–313 | 0.25 |
| | | | | | 313–305 | 5 min |
| | | | | | 310 | 0.25 |
| Ex. 3 | Trimer | 0.35, 333 | MeBuImT | 5.29 | 260 | 0.5 |
| Ex. 4 | Tetramer>> Trimer | 0.35, 250 | MeBuImT | 5.29 | 260–270 | 0.25 |
| | | | | | 305–313 | 0.25 |
| | | | | | 313–305 | 5 min |
| | | | | | 310 | 0.25 |
| Ex. 5 | Trimer | 0.175, 166 | MeBu ImT/ $\phi$PH(OH) (O) | 2, 11.8 1.5, 9.5 | 275 265–271 282–289 | <1.5 3.5 3.5 |
| Ex. 6 | Trimer | 0.175, 166 | MeBu ImT/ 0PH(OH) (O) | 2, 11.8 1.8, 11.4 | 260 288 | 1.25 2.75 |
| Ex. 7 | Trimer | 0.175, 166 | MeBu ImT/ $\phi$PH(OH) (O) | 2, 11 1.5, 9.5 | 275 290 | 5.5 0.75 |
| Ex. 8 | Trimer | 0.174, 166 | MeBu ImT/ PyEPO$_3$H | 2, 11.76 1.8, 9.5 | 283 295 | 1 1.5 |
| Ex. 9 | Dimer + Trimer 3 > 2 | 0.14 | $\phi$PH(OH) (O) | 1.5, 9.5 | 275 | 6 |
| Ex. 10 | 3 | 0.087 | (NH$_2$)$_2$C=S | 2, 26 | 275 | 6 |
| Ex. 11 | 3 | 0.087 | (NH$_2$)$_2$C=S $\phi$PH(OH) (O) | 2, 26 2, 13 | 275 | 6 |
| Ex. 12 Control | 3 —> 10 | 0.175, 166 | none | none | 275 | 6 |
| Ex. 12 | 3 —> 10 | 0.175, 166 | MeBu ImT/ $\phi$PH(OH) (O) | 2.0, 12 1.5, 9.5 | 275 | 6 |

| | Phase* | Yield g | Inh. Visc. H$_2$SO$_4$ | M$_w$ | M$_n$ | MWD |
|---|---|---|---|---|---|---|
| Ex. 1 | | | 0.058 | | | |
| Ex. 3 Control | m | | 0.09 | | | |
| Ex. 3 | m | 0.3 | 0.57 | 61100 78600 | 7410 48700 | 8.2 1.6 |
| Ex. 4 | m m-p p p | 0.23 | 0.22 | | | |
| Ex. 5 | m-s m | | 0.43 | 38200 | 9220 | 4.1 |

TABLE 1A-continued

| | | | |
|---|---|---|---|
| Ex. 6 | m-s<br>m-s<br>m-s | | 0.58 |
| Ex. 7 | m<br>m-s | | 0.82 |
| Ex. 8 | | 0.154 | 0.51 |
| Ex. 9 | m | 0.12 | 0.26 |
| Ex. 10 | m | 0.071 | |
| Ex. 11 | m | 0.04 | 0.53 |
| Ex. 12 Control | m | 0.14 | 0.26 |
| Ex. 12 | m —> s | 0.12 | 0.65 |

*m = melt
p = paste
s = solid

TABLE 1B

| | Comments On Entries in Table 1A |
|---|---|
| Example 1 | From Prep HPLC Structure by FABMS and $^1$H NMR. |
| Example 3 (Control) | Very low conversion (TLC). |
| Example 3 | Incomplete conversion. TLC analysis indicates cyclic trimer and oligomer present in product. $M_w$ and $M_n$ calculated when 30 wt % low MW fraction discounted from GPC. |
| Example 4 | The cyclic tetramer used in this experiment contained significant cyclic trimer. TLC indicates incomplete conversion during polymerization. |
| Example 5 | Melt formed quickly upon heating at 275° C. Bath shut-off sometimes during next −1.5 h. During heating at 280° +C., melt became viscous and solidified. Foamy solid was isolated from stirrer and flexible film was found at bottom of flask. TLC of CHCl$_3$ fraction showed virtually complete conversion. |
| Example 6 | Fibers could be pulled from melt at 330° C. The brittle film obtained on pressing at 310° C. on a Carver press could be drawn −3x at 289° C. Orientation was evident by polarized light microscopy. |
| Example 7 | A tough film formed on wall of reactor during the polymerization which could be oriented by drawing. |
| Example 8 | — |
| Example 9 | TLC indicated appreciable conversion of cyclic dimer and trimer to polymer consistent with the inherent viscosity. Unconverted cyclic dimer and trimer were present in product. |
| Example 10 | TLC on brittle glassy product indicated some conversion to polymer but much cyclic trimer remaining. |
| Example 11 | TLC indicated presence of unconverted cyclic trimer, but as indicated by the inherent viscosity, the conversion was sided by the phenylphosphinic acid cocatalyst. |
| Example 12 (Control) | Mixture of cyclic oligomers from HPLC was dried under pump vacuum in Abderhalden drying apparatus using toluene vapor bath. Product was brittle glass. |
| Example 12 | Cyclic oligomers dried same as above. Homogeneous Melt solidified during polymerization giving a bead of polymer with a pearlescent surface and a clear center. |

Although preferred embodiments of the invention have been described hereinabove, it is to be understood that there is no intention to limit the invention to the precise constructions herein disclosed and it is to be further understood that the right is reserved to all changes coming within the scope of the invention as defined by the appended claims.

We claim:

1. A compound of the formula:

wherein A, B, D, and E, are independently selected from the group consisting of benzene or benzene derivatives where the substituents on the benzene are alkyl of 1 to about 8 carbon atoms, halide, or alkoxy of 1 to about 8 carbon atoms 3,3'-biphenylene, 4,4'-biphenylene, 1,4-naphthalenediyl, 2,6-naphthalenediyl, oxy-3,4'-diphenyldiyl, oxy-4,4'-diphenyldiyl, methylene-3,4'-diphenyldiyl, methylene-4,4'-diphenyldiyl, sulfonyl-3,4'-diphenyldiyl, and sulfonyl-4,4'-diphenyldiyl; R is alkyl of 1 to about 8 carbon atoms or cycloalkyl of 3 to about 8 carbon atoms or aralkyl with ar- being phenyl or naphthyl and the alkyl portion of 1 to about 8 carbon atoms; and n is an integer from 0 to about 12.

2. The compound according to claim 1 of the formula:

wherein R is alkyl of 1 to about 8 carbon atoms or cycloalkyl of 3 to about 8 carbon atoms or aralkyl with ar- being phenyl or naphthyl and the alkyl portion of 1 to about 8 carbon atoms; and X is hydrogen, alkyl of 1 to about 8 carbon atoms, halide, or alkoxy of 1 to about 8 carbon atoms, Y is defined the same as is X, and n is an integer ranging from 0 to about 12.

3. A process for the preparation of the compound of claim 1 consisting of reacting monomeric components of the structures ClCO-A-COCl and ClCO-D-COCl with monomeric components of the formulas RHN-B-NHR and RHN-E-NHR wherein:

A, B, D and E, are independently selected from the group consisting of benzene or benzene derivatives where the substituents on the benzene are alkyl of 1 to about 8 carbon atoms, halide, or alkoxy of 1 to about 8 carbon atoms, 3,3'-biphenylene, 4,4'-biphenylene, 1,4-naphthalenediyl, 2,6-naphthalenediyl, oxy-3,4'-diphenyldiyl, oxy-4,4'-diphenyldiyl, methylene-3,4'-diphenyldiyl, methylene-4,4'-diphenyldiyl, sulfonyl-3,4'-diphenyldiyl, and sulfonyl-4,4'-diphenyldiyl and R is alkyl of 1 to about 8 carbon atoms or cycloalkyl of 3 to about 8 carbon atoms or aralkyl with ar- being phenyl or naphthyl and the alkyl portion of 1 to about 8 carbon atoms; in the presence of an aprotic organic solvent; and carried out within a temperature range of about 40° C. to about 300° C.

4. The process of claim 3 carried out in the presence of a tertiary amine base selected from triethyl amine, pyridine and 4-4-dimethylaminopyridine.

5. The process of claim 4 wherein the tertiary amine base is 4-dimethylaminopyridine.

6. The process of claim 3 wherein R has 3 to 8 carbon atoms.

7. The process of claim 6 wherein R has 4 to 6 carbon atoms.

8. The process of claim 6 wherein R is s-butyl.

9. The process of claim 3 wherein the aprotic solvent is selected from toluene, xylene, o-dichlorobenzene, 1,3,5-trichlorobenzene, tetrahydrofuran and methylene chloride.

10. The process of claim 9 wherein the solvent is dichlorobenzene.

11. The process of claim 3 carried out within a temperature range of about 100° C. to about 200° C.

12. A process for the preparation of compounds of the formula of claim 1, which process consists of reacting 2 or more monomeric components of the formula ClCO-Q-NHR wherein Q is A, B, C, D or E wherein A, B, D and E, are independently selected from the group consisting of benzene or benzene derivatives where the substituents on the benzene are alkyl of 1 to about 8 carbon atoms, halide, or alkoxy of 1 to about 8 carbon atoms, 3,3'-biphenylene, 4,4'-biphenylene, 1,4-naphthalenediyl, 2,6-naphthalenediyl, oxy-3,4'-diphenyldiyl, oxy-4,4'-diphenyldiyl, methylene-3,4'-diphenyldiyl, methylene-4,4'-diphenyldiyl, sulfonyl-3,4'-diphenyldiyl, and sulfonyl-4,4'-diphenyldiyl and R is alkyl of 1 to about 8 carbon atoms or cycloalkyl of 3 to about 8 carbon atoms or aralkyl with ar- being phenyl or naphthyl and the alkyl portion of 1 to about 8 carbon atoms, in the presence of an aprotic organic solvent, carried out within a temperature range of about 40° C. to about 300° C. and in the presence of a nucleophilic catalyst.

13. The process of claim 12 wherein R has 3 to 8 carbon atoms.

14. The process of claim 13 wherein R has 4 to 6 carbon atoms.

15. The process of claim 13 wherein R is s-butyl.

16. The process of claim 12 wherein the aprotic solvent is selected from toluene, xylene, o-dichlorobenzene, 1,3,5-trichlorobenzene, tetrahydrofuran and methylene chloride.

17. The process of claim 16 wherein the solvent is dichlorobenzene.

18. The process of claim 12 carried out within a temperature range of about 100° C. to about 200° C.

19. A compound of the formula:

II wherein A and B, are independently, selected from the group consisting of benzene or benzene derivatives where the substituents on the benzene are alkyl of 1 to about 8 carbon atoms, halide, or alkoxy of 1 to about 8 carbon atoms, 3,3'-biphenylene, 4,4'-biphenylene, 1,4-naphthalenediyl, 2,6-naphthalenediyl, oxy-3,4'-diphenyldiyl, oxy-4,4'-diphenyldiyl, methylene-3,4'-diphenyldiyl, methylene-4,4'-diphenyldiyl, sulfonyl-3,4'-diphenyldiyl, and sulfonyl-4,4'-diphenyldiyl; R is alkyl of 1 to about 8 carbon atoms or cycloalkyl of 3 to about 8 carbon atoms or aralkyl with ar- being phenyl or naphthyl and the alkyl portion of 1 to about 8 carbon atoms; and n is an integer from 1 to 12.

20. The cyclic oligomer of claim 19 wherein A and B, are independently selected from the group consisting of p-phenylene, m-phenylene, 3,3'-biphenylene, 4,4'-biphenylene, 1,4-naphthalenediyl, 2,6-naphthalenediyl, oxy-3,4'- and oxy-4,4'-diphenyldiyl and their corresponding methyl and sulfonyl analogs thereof.

* * * * *